United States Patent
Hoshino

(10) Patent No.: US 8,558,024 B2
(45) Date of Patent: Oct. 15, 2013

(54) FLUORINATED COMPOUND AND FLUORINATED POLYMER

(75) Inventor: Taiki Hoshino, Tokyo (JP)

(73) Assignee: Asahi Glass Company, Limited, Tokyo (JP)

(*) Notice: Subject to any disclaimer, the term of this patent is extended or adjusted under 35 U.S.C. 154(b) by 0 days.

(21) Appl. No.: 13/435,189

(22) Filed: Mar. 30, 2012

(65) Prior Publication Data

US 2012/0190809 A1 Jul. 26, 2012

Related U.S. Application Data

(63) Continuation of application No. PCT/JP2010/069516, filed on Nov. 2, 2010.

(30) Foreign Application Priority Data

Nov. 2, 2009 (JP) ................................ 2009-252411

(51) Int. Cl.
*C07C 69/00* (2006.01)

(52) U.S. Cl.
USPC ........... 560/138; 560/145; 560/219; 560/221; 560/229; 570/127; 570/128; 570/131; 526/242; 526/246

(58) Field of Classification Search
USPC .......... 560/138, 145, 219, 229; 570/127, 128, 570/130
See application file for complete search history.

(56) References Cited

U.S. PATENT DOCUMENTS

| | | | | |
|---|---|---|---|---|
| 5,087,672 A | * | 2/1992 | Babirad et al. | 525/329.5 |
| 5,814,378 A | * | 9/1998 | Onishi et al. | 428/1.3 |
| 6,730,241 B2 | * | 5/2004 | Obi et al. | 252/299.67 |
| 6,824,709 B2 | * | 11/2004 | Shundo | 252/299.62 |
| 2005/0007541 A1 | * | 1/2005 | Sasada et al. | 349/183 |
| 2010/0304148 A1 | * | 12/2010 | Hirai et al. | 428/412 |

FOREIGN PATENT DOCUMENTS

| DE | 4434976 | | 4/1996 |
|---|---|---|---|
| JP | 2003213265 A | * | 7/2003 |
| JP | 2009-031502 | | 2/2009 |
| WO | WO 02/083809 | | 10/2002 |
| WO | WO 2004/035708 | | 4/2004 |

OTHER PUBLICATIONS

Machine translation of JP 2003-213265 A, Oct. 3, 2012.*
International Search Report issued Jan. 25, 2011 in PCT/JP2010/069516 filed Nov. 2, 2010.

* cited by examiner

*Primary Examiner* — Nicole M Buie-Hatcher
(74) *Attorney, Agent, or Firm* — Oblon, Spivak, McClelland, Maier & Neustadt, L.L.P.

(57) ABSTRACT

To provide a fluorinated compound having an $R^F$ group with at most 6 carbon atoms, whereby a fluorinated polymer having a highly durable water/oil repellency can be produced, and an environmental load is little, and a fluorinated polymer having a highly durable water/oil repellency and presenting little environmental load, obtainable by polymerizing such a fluorinated compound. A fluorinated compound represented by the following formula (I) and its polymer:

$$CH_2=C(M)COO(CH_2)_n PhXPhZC_r F_{2r+1} \quad (I)$$

(in the formula (I), M is a hydrogen atom, a methyl group or a halogen atom, n is an integer of from 0 to 2, Ph is a phenylene group, X is $CH_2O$ or $OCH_2$, Z is a single bond, a $C_{1-4}$ alkylene group containing an etheric oxygen atom, or $COO(CH_2)_m$ (wherein m is an integer of from 1 to 4), and r is an integer of from 1 to 6).

10 Claims, No Drawings

FLUORINATED COMPOUND AND FLUORINATED POLYMER

TECHNICAL FIELD

The present invention relates to a novel fluorinated compound and a fluorinated polymer obtainable by polymerizing it.

BACKGROUND ART

As a technique to simultaneously impart water repellency and oil repellency to a surface, it is known to treat an article with an organic solvent solution or aqueous dispersion of a polymer comprising polymerized units of a polymerizable monomer containing a polyfluoroalkyl group (a group having a structure wherein at least two and at most all of hydrogen atoms in an alkyl group are substituted by fluorine atoms, such a polyfluoroalkyl group will be hereinafter referred to as an "$R^f$ group") in its molecule, or a copolymer of such a monomer with another monomer.

Such water/oil repellency is attributable to formation of "a low surface energy surface" having a low critical surface tension on the surface due to a surface orientation of $R^f$ groups on the coating film. It has been taken for granted that in order to attain both water repellency and oil repellency, orientation of $R^f$ groups at the surface is important, and in order to realize the surface orientation of $R^f$ groups, it is necessary to have constituting units derived from a monomer having a perfluoroalkyl group (a group having a structure wherein all of hydrogen atoms in an alkyl group are substituted by fluorine atoms, such a perfluoroalkyl group will be hereinafter referred to as an "$R^F$ group") with at least 8 carbon atoms in the polymer.

However, recently, EPA (Environmental Protection Agency in U.S.A.) has pointed out that a compound having an $R^F$ group with at least 8 carbon atoms is likely to be decomposed in vivo and in the environment, and the decomposed product is likely to be accumulated, i.e. its environment load is high. Therefore, a copolymer for a water/oil repellent composition is required, which has constituting units derived from a monomer having an $R^F$ group with at most 6 carbon atoms and containing no structural units derived from a monomer having an $R^F$ group with at least 8 carbon atoms.

However, in the case of a monomer having an $R^f$ group with at most 6 carbon atoms, as compared with a monomer having an $R^f$ group with at least 8 carbon atoms, the $R^f$ orientation at the surface tends to be weak, and the water/oil repellency tends to be low. It is known to increase the water/oil repellency even in the case of a monomer having an $R^f$ group with at most 6 carbon atoms, by copolymerizing it with a monomer not having an $R^f$ group and having a high microcrystallite melting point (Patent Document 1), or copolymerizing it with a monomer having a crosslinkable functional group and not having an $R^f$ group (Patent Document 2).

On the other hand, with a polymer composed solely of a monomer having an $R^f$ group with at most 6 carbon atoms, it has been so far impossible to impart a sufficient water/oil repellency and excellent durability thereof.

Therefore, with respect to a monomer having an $R^f$ group with at most 6 carbon atoms, particularly an $R^F$ group with at most 6 carbon atoms, a monomer and its polymer have been desired, whereby by polymerizing such a monomer, it is possible to obtain a polymer having a highly durable water/oil repellency.

PRIOR ART DOCUMENTS

Patent Documents
Patent Document 1: WO02/083809
Patent Document 2: WO04/035708

DISCLOSURE OF INVENTION

Technical Problem

It is an object of the present invention to provide a fluorinated compound having an $R^F$ group with at most 6 carbon atoms, whereby a fluorinated polymer having a highly durable water/oil repellency can be produced, and an environmental load is little, and a fluorinated polymer having a highly durable water/oil repellency and presenting little environmental load, obtainable by polymerizing such a fluorinated compound.

Solution to Problem

The present invention provides the following.

(1) A fluorinated compound represented by the following formula (I):

$$CH_2=C(M)COO(CH_2)_nPhXPhZC_rF_{2r+1} \quad (I)$$

(in the formula (I), M is a hydrogen atom, a methyl group or a halogen atom, n is an integer of from 0 to 2, Ph is a phenylene group, X is $CH_2O$ or $OCH_2$, Z is a single bond, a $C_{1-4}$ alkylene group containing an etheric oxygen atom, or COO$(CH_2)_m$ (wherein m is an integer of from 1 to 4), and r is an integer of from 1 to 6).

(2) The fluorinated compound according to the above (1), wherein Ph in the formula (I) is a 1,4-phenylene group.

(3) The fluorinated compound according to the above (1) or (2), wherein r in the formula (I) is an integer of from 2 to 6.

(4) The fluorinated compound according to the above (3), wherein r in the formula (I) is an integer of from 4 to 6.

(5) The fluorinated compound according to the above (1), wherein the fluorinated compound represented by the formula (I) is a compound represented by any one of the following formulae (I-1) to (I-5):

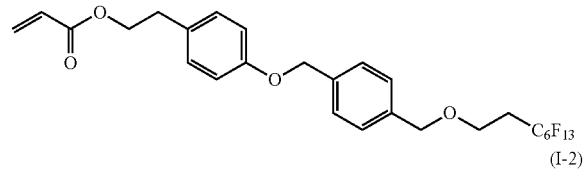

(I-1)

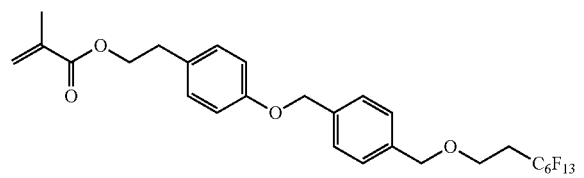

(I-2)

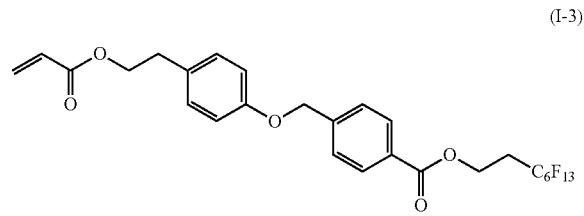

(I-3)

(I-4)

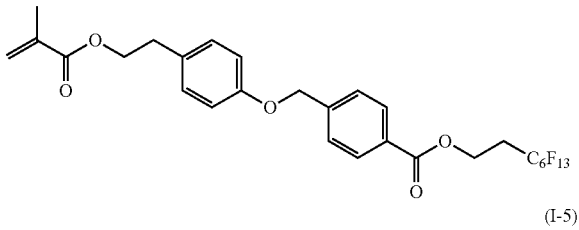

(I-5)

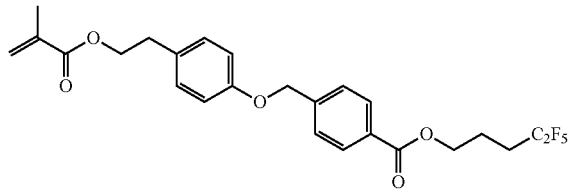

(6) The fluorinated compound according to any one of the above (1) to (5), wherein in the formula (I), r is an integer of from 4 to 6, and $C_rF_{2r+1}$ is linear.

(7) A fluorinated polymer obtainable by polymerizing one member selected from the fluorinated compound as defined in any one of the above (1) to (6).

(8) The fluorinated polymer according to the above (7), which has a mass average molecular weight (Mw) of from 2,000 to 1,000,000.

(9) The fluorinated polymer according to the above (8), which has a mass average molecular weight (Mw) of from 5,000 to 500,000.

Advantageous Effects of Invention

By using the fluorinated compound of the present invention, it is possible to produce a fluorinated polymer having a highly durable water/oil repellency and presenting little load to the environment. Further, the fluorinated polymer of the present invention has a highly durable water/oil repellency and presents little load to the environment.

DESCRIPTION OF EMBODIMENTS

Now, embodiments of the present invention will be described. In this specification, a (meth)acrylate means an acrylate or a methacrylate. Likewise, (meth)acrylic acid means acrylic acid or methacrylic acid.

<Fluorinated Compound of the Present Invention>

The fluorinated compound of the present invention is a fluorinated compound which, as shown in the following formula (I), has an acryloyloxy group (which may be substituted) as a polymerizable group at its one terminal and an $R^F$ group with at most 6 carbon atoms at the other terminal and which has, as a bivalent linking group to link the two, a linking group of a structure having two benzene rings bonded by a group containing an etheric oxygen atom. A fluorinated polymer obtainable by polymerizing the fluorinated compound of the present invention having such a molecular structure, has a water/oil repellency and also has a high durability whereby the water/oil repellency will not be impaired by e.g. use for a long period of time.

$$CH_2=C(M)COO(CH_2)_nPhXPhZC_rF_{2r+1} \quad (I)$$

(in the formula (I), M is a hydrogen atom, a methyl group or a halogen atom, n is an integer of from 0 to 2, Ph is a phenylene group, X is $CH_2O$ or $OCH_2$, Z is a single bond, a $C_{1-4}$ alkylene group containing an etheric oxygen atom, or $COO(CH_2)_m$ (wherein m is an integer of from 1 to 4), and r is an integer of from 1 to 6).

In the above formula (I), M is a hydrogen atom, a methyl group or a halogen atom, specifically a halogen atom such as F, Cl, Br or the like, but preferred M is a hydrogen atom or a methyl group, and more preferred M is a methyl group. In a case where M is a hydrogen atom, the obtainable polymer has water/oil repellency and is particularly excellent in durability for maintaining such water/oil repellency. In a case where M is a methyl group, the obtainable polymer is particularly excellent in the initial water/oil repellency and excellent also in the durability for maintaining it.

In the above formula (I), n is an integer of from 0 to 2, but a preferred number of n is 1 or 2. When the number of n is 1 or 2, the raw material is readily available, such being desirable. In the above formula (I), each of two Ph is a phenylene group. So long as it is a phenylene group, it may be any one of a 1,2-phenylene group, a 1,3-phenylene group and a 1,4-phenylene group. However, in the present invention, from the viewpoint of the availability of the raw material, it is preferred that both of two Ph are 1,4-phenylene groups.

Further, in the above formula (I), X is $CH_2O$ or $OCH_2$, preferably $OCH_2$.

In the above formula (I), Z is a single bond, a $C_{1-4}$ alkylene group containing an etheric oxygen atom, or $COO(CH_2)_m$ (wherein m is an integer of from 1 to 4). In a case where Z is a $C_{1-4}$ alkylene group containing an etheric oxygen atom, Z may preferably be $—(CH_2)_p—O—(CH_2)_q—$ (wherein p an integer of is from 0 to 2, and q is an integer of from 1 to 4, provided that p+q=1 to 4). The reason as to why such a group is preferred as Z is that the raw material is readily available.

Further, in the above formula (I), r is an integer of from 1 to 6. When r is within a range of from 1 to 6, the obtainable polymer exhibits water/oil repellency. However, in order to obtain higher water/oil repellency, r is preferably from 2 to 6, more preferably from 4 to 6.

In the present invention, among fluorinated compounds represented by the above formula (I), a compound represented by any one of the following formulae (I-1) to (I-5) is particularly preferred.

(I-1)

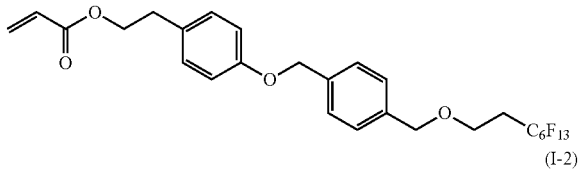

(I-2)

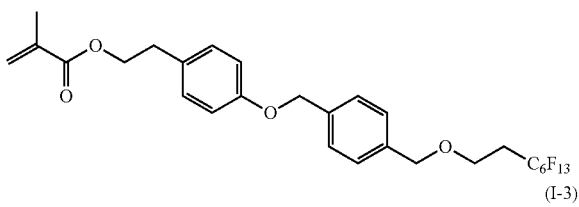

(I-3)

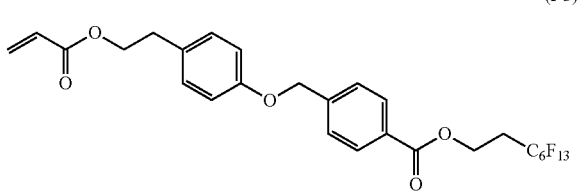

-continued (I-4)

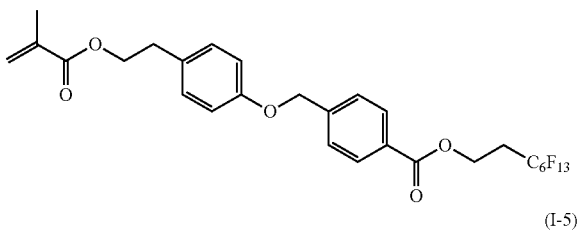

(I-5)

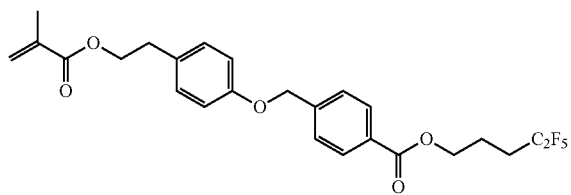

In the present invention, it is preferred that in the above formula (I), r is an integer of from 4 to 6, and $C_rF_{2r+1}$ is linear. Further, the $R^F$ group in the above formulae (I-1) to (I-4) is preferably linear.

<Production Method>

In the present invention, a method for producing the fluorinated compound represented by the above formula (I) is not particularly limited. As a method for producing the fluorinated compound represented by the above formula (I), specifically, the following production methods may, respectively, be mentioned for the following respective compounds (i) to (iii) which are different in Z in the formula (I).

Fluorinated compound (i) of the above formula (I) wherein Z is a $C_{1-4}$ alkylene group containing an etheric oxygen atom Fluorinated compound (ii) of the above formula (I) wherein Z is $COO(CH_2)_m$ (wherein m is an integer of from 1 to 4)

Fluorinated compound (iii) of the above formula (I) wherein Z is a single bond (1) Method for producing fluorinated compound (i) of the above formula (I) wherein Z is a $C_{1-4}$ alkylene group containing an etheric oxygen atom The above fluorinated compound (i) can be produced, for example, by carrying out reactions 1-1 to 1-3 which will be described below, although not limited thereto. Here, in the following production process, identification or confirmation of the obtainable intermediate substances or desired substances may be carried out by common methods such as measurement $^1$H-NMR, FT-IR, elemental analyses, etc. Further, also in the case of producing the fluorinated compound (ii) in the after-described (2), identification or confirmation of the obtainable intermediate substances or desired substances may be carried out by similar methods.

<Reaction 1-1>

Using, as a starting material, a compound represented by the formula $Y^1CH_2Ph(CH_2)_pY^2$ (wherein each of $Y^1$ and $Y^2$ which are independent of each other, is Cl, Br or I), a compound (A) is obtained by reacting a compound having an $R^F$ group (perfluoroalkyl group) with at most 6 carbon atoms thereto, as shown by the following reaction formula.

$$Y^1CH_2Ph(CH_2)_pY^2+C_rF_{2r+1}(CH_2)_qOH \rightarrow Y^1CH_2Ph(CH_2)_pO(CH_2)_qC_rF_{2r+1} \quad (A)$$

(wherein p is an integer of from 0 to 2, and q is an integer of from 1 to 4, provided p+q=1 to 4).

The above reaction 1-1 is preferably carried out in the presence of an alkali. As the alkali, sodium hydroxide or potassium hydroxide may, for example, be used. The reaction 1-1 is preferably carried out in a solvent, and as such a solvent, specifically, acetonitrile, N,N-dimethylformamide (DMF) or water may, for example, be mentioned.

Specifically, the reaction 1-1 is carried out under the following preferred reaction conditions, by mixing the alkali (such as sodium hydroxide) in a proportion of from 5 to 50 parts by mass and the solvent in a proportion of from 50 to 5,000 parts by mass, to 100 parts by mass in a total amount of the above starting material and the compound having an $R^F$ group with at most 6 carbon atoms.

As the reaction conditions, preferably, conditions such as reaction container: made of glass, made of SUS, etc., temperature: from 50 to 150° C., pressure: from 0 to 5 MPa, time: from 1 to 100 hours, etc. may be mentioned. Here, the pressure condition is not the absolute pressure in the reaction and represents the range of pressure to be used for pressurizing or depressurizing. Hereinafter, the same applies to the reaction pressure condition in this specification.

As a method for purifying the compound (A) from the reaction crude liquid containing the compound (A) thus obtained, a method may, for example, be mentioned wherein the solvent is distilled off from the reaction crude liquid, and the solid is filtered off, followed by distillation for purification.

<Reaction 1-2>

A compound (B) is obtained by reacting a compound having a benzene ring to the compound (A) obtained in the above reaction 1-1, as shown by the following reaction formula.

$$Y^1CH_2Ph(CH_2)_pO(CH_2)_qC_rF_{2r+1}+ \\ HO(CH_2)_nPhOH \rightarrow HO(CH_2)_n \\ PhOCH_2Ph(CH_2)_pO(CH_2)_qC_rF_{2r+1} \quad (B)$$

The above reaction 1-2 is preferably carried out in the presence of an alkali. As the alkali, potassium carbonate, sodium carbonate or triethylamine may, for example, be used. The reaction 1-2 is preferably carried out in a solvent, and as such a solvent, specifically, N,N-dimethylformamide (DMF), acetonitrile, acetone or 2-butanone may, for example, be used.

Specifically, the reaction 1-2 is carried out under the following preferred reaction conditions, by mixing the alkali (such as potassium carbonate) in a proportion of from 10 to 100 parts by mass, and the solvent in a proportion of from 50 to 5,000 parts by mass, to 100 parts by mass in a total amount of the above compound (A) and the compound having a benzene ring.

As the reaction conditions, preferably, conditions such as reaction container: made of glass, made of SUS, etc., temperature: from 30 to 100° C., pressure: from 0 to 1 MPa, time: from 1 to 24 hours, etc. may be mentioned.

As a method for purifying the compound (B) from the reaction crude liquid containing the compound (B) thus obtained, a method may, for example, be mentioned wherein chloroform, methylene chloride, ethyl acetate, dichloropentafluoropropane or the like is added to the reaction crude liquid, the mixture is washed a few times with a sufficient amount of distilled water, then the solvent is distilled off and further, the residue is recrystallized from a suitable solvent such as methanol/hexane, or methanol.

<Reaction 1-3>

A fluorinated compound (i) which is the fluorinated compound (I) of the present invention wherein Z is a $C_{1-4}$ alkylene group containing an etheric oxygen atom, is obtained by reacting a (meth)acrylic acid compound to the compound (B)

obtained in the above reaction 1-2, as shown by the following reaction formula.

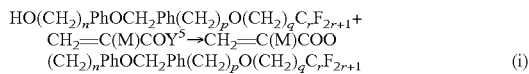

$$HO(CH_2)_nPhOCH_2Ph(CH_2)_pO(CH_2)_qC_rF_{2r+1} + CH_2=C(M)COY^5 \rightarrow CH_2=C(M)COO(CH_2)_nPhOCH_2Ph(CH_2)_pO(CH_2)_qC_rF_{2r+1} \quad (i)$$

(In the reaction formula, $Y^5$ is Cl, a hydroxy group or an alkoxy group.)

In the above reaction 1-3, in the case of reacting a compound wherein $Y^5$ is Cl i.e. (meth)acrylic acid chloride, as the (meth)acrylic acid compound, to the compound (B) obtained by the above reaction 1-2, such a reaction is preferably carried out in the presence of an alkali. As the alkali, triethylamine, potassium carbonate or sodium hydroxide may, for example, be used. In such a case, the reaction 1-3 is preferably carried out in a solvent, and as such a solvent, specifically, dichloropentafluoropropane, acetone, 2-butanone, ethyl acetate, methylene chloride, chloroform, pyridine or water may, for example, be mentioned.

Specifically, in the case of using (meth)acrylic acid chloride as the (meth)acrylic acid compound, the above reaction 1-3 is carried out under the following preferred reaction conditions by mixing the alkali (such as triethylamine) in a proportion of from 25 to 100 parts by mass and the solvent in a proportion of from 50 to 5,000 parts by mass, and further, as the case requires, a suitable amount of the polymerization inhibitor such as hydroquinone, to 100 parts by mass in total of the above compound (B) and the (meth)acrylic acid chloride. In a case where the solvent is pyridine, pyridine serves as an alkali, and therefore, it is not necessary to add an alkali. In a case where the solvent is water (Schotten-Baumann reaction), a catalyst such as N-methylimidazole or 4-(dimethylamino)pyridine may be used, as the case requires.

As the reaction conditions, preferably, conditions such as reaction container: made of glass, made of SUS, etc., temperature: from 0 to 40° C., pressure: from 0 to 1 MPa, atmosphere: gas substitution by nitrogen, argon or the like, time: from 1 to 24 hours, etc. may be mentioned.

In the above reaction 1-3, in the case of reacting a compound wherein $Y^5$ is a hydroxy group or an alkoxy group, as the (meth)acrylic acid compound, to the compound (B) obtained in the above reaction 1-2, for such a reaction, sulfuric acid or 4-toluenesulfonic acid monohydrate may, for example, be used as a catalyst. In such a case, the reaction 1-3 may be carried out in the absence of a solvent or in a solvent, and as such a solvent, specifically, toluene or 2-butanone may, for example, be mentioned.

Specifically, the above reaction 1-3 in the case of using a compound wherein $Y^5$ is a hydroxy group or an alkoxy group, as the (meth)acrylic acid compound, is carried out under the following preferred reaction conditions by mixing the catalyst (such as sulfuric acid) in a proportion of from 0.01 to 10 parts by mass and the solvent in a proportion of from 0 to 5,000 parts by mass, and further, as the case requires, a suitable amount of a polymerization inhibitor such as hydroquinone, to 100 parts by mass in total of the above compound (B) and the (meth)acrylic acid compound.

As the reaction conditions, preferably, conditions such as reaction container: made of glass, made of SUS, etc., temperature: from 50 to 150° C., pressure: from −0.1 to 1 MPa, atmosphere: gas substitution by nitrogen, argon or the like, time: from 1 to 100 hours, etc. may be mentioned. Further, it is preferred to carry out the reaction, while distilling reaction byproducts off, as the case requires.

As a method for purifying the fluorinated compound (i) from the reaction crude liquid containing the fluorinated compound (i) thus obtained, a method may, for example, be mentioned wherein after washing the reaction crude liquid a few times with a sufficient amount of distilled water, the solvent is distilled off.

Here, in the above-described fluorinated compound (i), the linking group X to link between the two Ph is $OCH_2$, but in order to make X to be $CH_2O$, the starting material to be used in the above reaction 1-1 is made to be a compound represented by the formula $Y^6Ph(CH_2)_pY^2$ (wherein $Y^6$ is a hydroxy group or a hydroxy group protected by e.g. tetrahydrofuran), and after the above reaction 1-1, in a case where $Y^6$ is a hydroxy group protected by e.g. tetrahydrofuran, it is converted to a hydroxy group, and the compound having a benzene ring to be used in the above reaction 1-2 is made to be $HO(CH_2)_nPhCH_2Y^7$ (wherein $Y^7$ is Cl, Br or I), and the reaction conditions may suitably be adjusted. Further, with respect to the following fluorinated compounds (ii) and (iii), in a similar manner, the linking group X to link between the two Ph can be made to be $CH_2O$.

(2) Method for producing fluorinated compound (ii) of the above formula (I) wherein Z is $COO(CH_2)_m$ (wherein m is an integer of from 1 to 4)

The above fluorinated compound (II) can be produced, for example, by carrying out reactions 2-1 to 2-3 which will be described below, although not limited thereto.

<Reaction 2-1>

Using, as a starting material, a compound represented by the formula $Y^1CH_2PhCOY^8$ (wherein $Y^1$ is Cl, Br or I, and $Y^8$ is Cl, a hydroxy group or an alkoxy group), a compound (C) is obtained by reacting a compound having an $R^F$ group (perfluoroalkyl group) with at most 6 carbon atoms thereto, as shown by the following reaction formula.

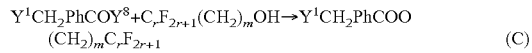

$$Y^1CH_2PhCOY^8 + C_rF_{2r+1}(CH_2)_mOH \rightarrow Y^1CH_2PhCOO(CH_2)_mC_rF_{2r+1} \quad (C)$$

In the above reaction 2-1, in the case of using, as the starting material, a compound wherein $Y^8$ is Cl i.e. an acid chloride, such a reaction is preferably carried out in the presence of an alkali. As the alkali, triethylamine, potassium carbonate or sodium hydroxide may, for example, be used. In such a case, the reaction 2-1 is preferably carried out in a solvent, and as such a solvent, specifically, acetone, 2-butanone, acetonitrile, ethyl acetate, methylene chloride, chloroform, pyridine or water may, for example, be mentioned.

Specifically, in the case of using an acid chloride wherein $Y^8$ is Cl, as the starting material, the above reaction 2-1 is carried out under the following preferred reaction conditions by mixing the alkali (such as triethylamine) in a proportion of from 25 to 100 parts by mass, and the solvent in a proportion of from 50 to 5,000 parts by mass, to 100 parts by mass in total of the above starting material and the compound having an $R^F$ group with at most 6 carbon atoms. In a case where the solvent is pyridine, pyridine serves also as an alkali, and therefore, it is not required to add an alkali. In a case where the solvent is water (Schotten-Baumann reaction), a catalyst such as N-methylimidazole or 4-(dimethylamino)pyridine may be used, as the case requires.

As the reaction conditions, preferably, conditions such as reaction container: made of glass, made of SUS, etc., temperature: from 0 to 40° C., pressure: from 0 to 1 MPa, atmosphere: gas substitution by nitrogen, argon or the like, time: from 1 to 24 hours, etc. may be mentioned.

In the above reaction 2-1, in a case where a compound wherein $Y^8$ is a hydroxy group or an alkoxy group is used as the starting material, for such a reaction, sulfuric acid or p-toluenesulfonic acid may, for example, be used as the catalyst. In such a case, the reaction 2-1 is carried out in the absence of a solvent or in a solvent, and as such a solvent, specifically, toluene or 2-butanone may, for example, be mentioned.

Specifically, in the case of using a compound wherein $Y^8$ is a hydroxy group or an alkoxy group, as the starting material, the above reaction 2-1 is carried out under the following preferred reaction conditions by mixing the catalyst (such as sulfuric acid) in a proportion of from 0.01 to 10 parts by mass, and the solvent in a proportion of from 0 to 5,000 parts by mass, to 100 parts by mass in total of the above starting material and the compound having an $R^F$ group with at most 6 carbon atoms.

As the reaction conditions, preferably, conditions such as reaction container: made of glass, made of SUS, etc., temperature: from 50 to 150° C., pressure: from −0.1 to 1 MPa, atmosphere: gas substitution by nitrogen, argon or the like, time: from 1 to 100 hours, etc. may be mentioned. Further, it is preferred to carry out the reaction while distilling reaction byproducts off, as the case requires.

As a method for purifying the compound (C) from the reaction crude liquid containing the compound (C) thus obtained, a method may, for example, be mentioned wherein to the reaction crude liquid, dichloropentafluoropropane, chloroform, ethyl acetate or the like is added, followed by washing a few times with a sufficient amount of distilled water, and then, the solvent is distilled off.

<Reaction 2-2>

A compound (D) is obtained by reacting a compound having a benzene ring to the compound (C) obtained in the above reaction 2-1, as shown by the following reaction formula.

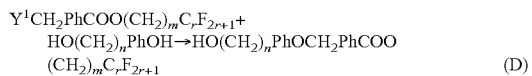

$$Y^1CH_2PhCOO(CH_2)_mC_rF_{2r+1} + HO(CH_2)_nPhOH \rightarrow HO(CH_2)_nPhOCH_2PhCOO(CH_2)_mC_rF_{2r+1} \quad (D)$$

The above reaction 2-2 is preferably carried out in the presence of an alkali. As the alkali, potassium carbonate, sodium carbonate or triethylamine may, for example, be used. The reaction 2-2 is preferably carried out in a solvent, and as such a solvent, specifically, N,N-dimethylformamide (DMF), acetonitrile, acetone or 2-butanone may, for example, be used.

Specifically, the reaction 2-2 is carried out under the following preferred reaction conditions by mixing the alkali (such as potassium carbonate) in a proportion of from 10 to 100 parts by mass, and the solvent in a proportion of from 50 to 5,000 parts by mass, to 100 parts by mass in total of the above compound (C) and the compound having a benzene ring.

As the reaction conditions, preferably, conditions such as reaction container: made of glass, made of SUS, etc., temperature: from 30 to 100° C., pressure: from 0 to 1 MPa, time: from 1 to 24 hours, etc. may be mentioned.

As a method for purifying the compound (D) from the reaction crude liquid containing the compound (D) thus obtained, a method may, for example, be mentioned wherein to the reaction crude liquid, chloroform, methylene chloride, ethyl acetate, dichloropentafluoropropane or the like is added, followed by washing a few times with a sufficient amount of distilled water, and then, the solvent is distilled off.

<Reaction 2-3>

A fluorinated compound (ii) which is the fluorinated compound (I) of the present invention wherein Z is $COO(CH_2)_m$ (wherein m is an integer of from 1 to 4), is obtained by reacting a (meth)acrylic acid compound to the compound (D) obtained in the above reaction 2-2, as shown by the following reaction formula.

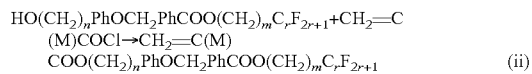

$$HO(CH_2)_nPhOCH_2PhCOO(CH_2)_mC_rF_{2r+1} + CH_2=C(M)COCl \rightarrow CH_2=C(M)COO(CH_2)_nPhOCH_2PhCOO(CH_2)_mC_rF_{2r+1} \quad (ii)$$

The above reaction 2-3 is preferably carried out in the presence of an alkali. As the alkali, triethylamine, potassium carbonate or sodium hydroxide may, for example, be used. The reaction 2-3 is preferably carried out in a solvent, and as such a solvent, specifically, methylene chloride, chloroform, acetone, 2-butanone, ethyl acetate, pyridine or water may, for example, be mentioned.

Specifically, the reaction 2-3 is carried out under the following preferred reaction conditions by mixing the alkali (such as triethylamine) in a proportion of from 25 to 100 parts by mass, and the solvent in a proportion of from 50 to 5,000 parts by mass, and further, as the case requires, a suitable amount of a polymerization inhibitor such as hydroquinone, to 100 parts by mass in total of the above compound (D) and the (meth)acrylic acid compound. In a case where the solvent is pyridine, pyridine serves also as an alkali, and therefore, it is not required to add an alkali. In a case where the solvent is water (Schotten-Baumann reaction), a catalyst such as N-methylimidazole or 4-(dimethylamino)pyridine may be used, as the case requires.

As the reaction conditions, preferably, conditions such as reaction container: made of glass, made of SUS, etc., temperature: from 0 to 40° C., pressure: from 0 to 1 MPa, atmosphere: gas substation by nitrogen, argon or the like, time: from 1 to 24 hours, etc. may be mentioned.

As a method for purifying the fluorinated compound (II) from the reaction crude liquid containing the fluorinated compound (II) thus obtained, a method may, for example, be mentioned wherein the reaction crude liquid is washed a few times with a sufficient amount of distilled water, then the solvent is distilled off, and further, the residue is recrystallized from a suitable solvent, such as methanol/dichloropentafluoropropane, methanol/chloroform, methanol or ethanol.

(3) Method for producing fluorinated compound (iii) of the above formula (I) wherein Z is a single bond The above fluorinated compound (iii) can be produced, for example, by carrying out reactions 3-1 to 3-3 which will be described below, although not limited thereto.

<Reaction 3-1>

Using, as a starting material, a compound represented by the formula $ClCH_2PhY^9$ (wherein $Y^9$ is Br or I), a compound (E) is obtained by reacting a compound having an $R^F$ group (perfluoroalkyl group) with at most 6 carbon atoms thereto, as shown by the following reaction formula.

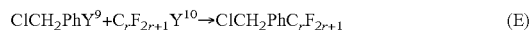

$$ClCH_2PhY^9 + C_rF_{2r+1}Y^{10} \rightarrow ClCH_2PhC_rF_{2r+1} \quad (E)$$

(In the reaction formula, $Y^{10}$ is Br Or I.)

In the above reaction 3-1, a reaction catalyst may be used as the case requires. As the reaction catalyst, copper may, for example, be preferably mentioned. Further, the reaction 3-1 is preferably carried out in a solvent, and as such a solvent, specifically, dimethylsulfoxide (DMSO) or DMF may, for example, be used.

Specifically, the reaction 3-1 is carried out under the following preferred reaction conditions by mixing the catalyst in a proportion of from 10 to 100 parts by mass, and a solvent in a proportion of from 50 to 5,000 parts by mass, to 100 parts by mass in total of the above starting material as the reaction material and the compound having an $R^F$ group with at most 6 carbon atoms.

As the reaction conditions, preferably, conditions such as reaction container: made of glass, made of SUS, etc., temperature: from 80 to 180° C., pressure: from 0 to 10 MPa, atmosphere: gas substitution by nitrogen, argon or the like, time: from 1 to 50 hours, etc. may be mentioned.

As a method for purifying the compound (E) from the reaction crude liquid containing the compound (E) thus obtained, a method may, for example, be mentioned wherein from the reaction crude liquid, the compound (E) is taken out by distillation and further washed a few times with a sufficient amount of distilled water, and the organic phase is separated.

<Reaction 3-2>

A compound (F) is obtained by reacting a compound having a benzene ring to the compound (E) obtained in the above reaction 3-1, as shown by the following reaction formula.

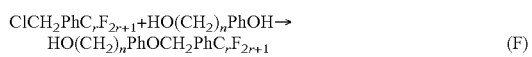

$$ClCH_2PhC_rF_{2r+1} + HO(CH_2)_nPhOH \rightarrow HO(CH_2)_nPhOCH_2PhC_rF_{2r+1} \quad (F)$$

The above reaction 3-2 is preferably carried out in the presence of an alkali. As the alkali, potassium carbonate, sodium carbonate or triethylamine may, for example, be used. The reaction 3-2 is preferably carried out in a solvent, and as such a solvent, specifically, N,N-dimethylformamide (DMF), acetonitrile, acetone or 2-butanone may, for example, be used.

Specifically, the reaction 3-2 is carried out under the following preferred reaction conditions by mixing the alkali (such as potassium carbonate) in a proportion of from 10 to 100 parts by mass, and the solvent in a proportion of from 50 to 5,000 parts by mass, to 100 parts by mass in total of the above compound (E) and the compound having a benzene ring.

As the reaction conditions, preferably, conditions such as reaction container: made of glass, made of SUS, etc., temperature: from 30 to 100° C., pressure: from 0 to 1 MPa, time: from 1 to 24 hours, etc. may be mentioned.

As a method for purifying the compound (F) from the reaction crude liquid containing the compound (F) thus obtained, a method may, for example, be mentioned wherein to the reaction crude liquid, chloroform, methylene chloride, ethyl acetate, dichloropentafluoropropane or the like is added, the mixture is washed a few times with a sufficient amount of distilled water, and then, the solvent is distilled off, and further, the residue is recrystallized from a suitable solvent such as methanol/hexane, or methanol.

<Reaction 3-3>

To the compound (F) obtained in the above reaction 3-2, a (meth)acrylic acid compound is reacted as shown by the following reaction formula, to obtain the fluorinated compound (iii) of the above formula (I) wherein Z is a single bond, among the fluorinated compound (I) of the present invention.

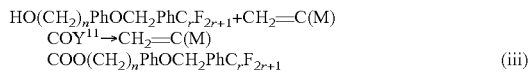

$$HO(CH_2)_nPhOCH_2PhC_rF_{2r+1} + CH_2=C(M)COY^{11} \rightarrow CH_2=C(M)COO(CH_2)_nPhOCH_2PhC_rF_{2r+1} \quad (iii)$$

(In the reaction formula, $Y^{11}$ is Cl, a hydroxy group or an alkoxy group.)

In the above reaction 3-3, in the case of reacting a compound wherein $Y^{11}$ is Cl, i.e. (meth)acrylic acid chloride, as the (meth)acrylic acid compound, to the compound (F) obtained in the above reaction 3-2, such a reaction is preferably carried out in the presence of an alkali. As the alkali, triethylamine, potassium carbonate or sodium hydroxide may, for example, be used. In such a case, the reaction 3-3 is preferably carried out in a solvent, and as such a solvent, specifically, dichloropentafluoropropane, acetone, 2-butanone, ethyl acetate, methylene chloride, chloroform, pyridine or water may, for example, be mentioned.

Specifically, in the case of using (meth)acrylic acid chloride as the (meth)acrylic acid compound, the above reaction 3-3 is carried out under the following preferred reaction conditions by mixing the alkali (such as triethylamine) in a proportion of from 25 to 100 parts by mass, and the solvent in a proportion of from 50 to 5,000 parts by mass, and further, as the case requires, a suitable amount of a polymerization inhibitor such as hydroquinone, to 100 parts by mass in total of the above compound (F) and the (meth)acrylic acid chloride. In a case where the solvent is pyridine, pyridine serves also as an alkali, and therefore, it is not required to add an alkali. In a case where the solvent is water (Schotten-Baumann reaction), a catalyst such as N-methylimidazole or 4-(dimethylamino)pyridine may be used, as the case requires.

As the reaction conditions, preferably, conditions such as reaction container: made of glass, made of SUS, etc., temperature: from 0 to 40° C., pressure: from 0 to 1 MPa, atmosphere: gas substitution by nitrogen, argon or the like, time: from 1 to 24 hours, etc. may be mentioned.

In the above reaction 3-3, in the case of reacting a compound wherein $Y^{11}$ is a hydroxy group or an alkoxy group, as the (meth)acrylic acid compound, to the compound (F) obtained in the above reaction 3-2, for such a reaction, sulfuric acid or 4-toluenesulfonic acid monohydrate may, for example, be used as a catalyst. In such a case, the reaction 3-3 is carried out in the absence of a solvent or in a solvent, and as such a solvent, specifically, toluene or 2-butanone may, for example, be mentioned.

Specifically, in the case of using the compound wherein $Y^{11}$ is a hydroxy group or an alkoxy group, as the (meth) acrylic acid compound, the above reaction 3-3 is carried out under the following preferred reaction conditions by mixing the catalyst (such as sulfuric acid) in a proportion of from 0.01 to 10 parts by mass, and the solvent in a proportion of from 0 to 5,000 parts by mass, and further, as the case requires, a suitable amount of a polymerization inhibitor such as hydroquinone, to 100 parts by mass in total of the above compound (F) and the (meth)acrylic acid compound.

As the reaction conditions, preferably, conditions such as reaction container: made of glass, made of SUS, etc., temperature: from 50 to 150° C., pressure: from −0.1 to 1 MPa, atmosphere: gas substitution by nitrogen, argon or the like, time: from 1 to 100 hours, etc. may be mentioned. Further, it is preferred to carry out the reaction while distilling reaction byproducts off, as the case requires.

As a method for purifying the fluorinated compound (iii) from the reaction crude liquid containing the fluorinated compound (iii) thus obtained, a method may, for example, be mentioned wherein the reaction crude liquid is washed a few times with a sufficient amount of distilled water, the organic layer is separated, and the solvent is distilled off.

<Polymer of the Present Invention>

The polymer of the present invention is a homopolymer obtainable by polymerizing one member selected from the above-described fluorinated compound of the present invention.

The polymer of the present invention preferably has a mass average molecular weight (Mw) of from 2,000 to 1,000,000, more preferably from 5,000 to 500,000. The polymer having a mass average molecular weight (Mw) within such a range is advantageous from the viewpoint of the durability of the water/oil repellency.

Here, the mass average molecular weight (Mw) of the polymer in this specification is a molecular weight calculated as a polymethyl methacrylate, which is measured by gel permeation chromatography (GPC).

As a method for polymerizing the fluorinated compound of the present invention, it is possible to employ a polymerization method such as an ion polymerization method or a radical polymerization. Particularly, a radical polymerization method is preferred in that the polymerization can be carried out under a mild condition by using a radical initiator as the polymerization initiator. Specifically, the radical polymerization can be carried out by using a polymerization method such as suspension polymerization, solution polymerization, bulk polymerization or emulsion polymerization.

Among these polymerization methods, in the production of the polymer according to the present invention, it is preferred to employ a polymerization method wherein the polymerization is carried out in a medium in the presence of a polymerization initiator, and a solution polymerization employing a solvent as the above medium, or an emulsion polymerization to be carried out by using a medium containing a surfactant and water, is more preferably used.

The production of the polymer is specifically one to polymerize the monomer in a medium in the presence of a polymerization initiator.

Further, in the production of the polymer, the monomer concentration in the medium is preferably from 5 to 50 vol %, more preferably from 20 to 40 vol %, by volume percentage of the monomer to the medium. As the medium, a halogen compound, a hydrocarbon, a ketone, an ester or an ether may, for example, be mentioned.

As the halogen compound, a halogenated hydrocarbon or a halogenated ether may, for example, be mentioned. As the halogenated hydrocarbon, a hydrochlorofluorocarbon or a hydrofluorocarbon may, for example, be mentioned.

As the hydrochlorofluorocarbon, $CH_3CCl_2F$, $CHCl_2CF_2CF_3$ or $CHClFCF_2CClF_2$ may, for example, be mentioned.

As the hydrofluorocarbon, $CF_3CHFCHFCF_2CF_3$, $CF_3(CF_2)_4CHF_2$, $CF_3CF_2CF_2CH_2CH_2CH_3$, $CF_3(CF_2)_5CH_2CH_3$ or 1,1,2,2,3,3,4-heptafluorocyclopentane may, for example, be mentioned.

As the halogenated ether, a hydrofluoroether may, for example, be mentioned.

As the hydrofluoroether, $CF_3CF_2CF_2CF_2OCH_3$, $(CF_3)_2CFCF_2OCH_3$, $CF_3CF_2CF_2CF_2OCH_2CH_3$, $(CF_3)CFCF_2OCH_2CH_3$, $CF_3CF_2CF(OCH_3)CF(CF_3)_2$, $CF_3CF_2CF(OCH_2CH_3)CF(CF_3)_2$, $C_3H_7OCF(CF_3)CF_2OCH_3$, $CHF_2CF_2OCH_2CF_3$ or $CF_3CF_2CH_2OCF_2CHF_2$ may, for example, be mentioned.

As the hydrocarbon, an aliphatic hydrocarbon, an alicyclic hydrocarbon or an aromatic hydrocarbon may, for example, be mentioned.

As the aliphatic hydrocarbon, pentane, 2-methylbutane, 3-methylpentane, hexane, 2,2-dimethylbutane, 2,3-dimethylbutane, heptane, octane, 2,2,4-trimethylpentane, 2,2,3-trimethylhexane, decane, undecane, dodecane, 2,2,4,6,6-pentamethylheptane, tridecane, tetradecane or hexadecane may, for example, be mentioned.

As the alicyclic hydrocarbon, cyclopentane, methylcyclopentane, cyclohexane, methylcyclohexane or ethylcyclohexane may, for example, be mentioned.

As the aromatic hydrocarbon, benzene, toluene or xylene may, for example, be mentioned.

As the ketone, acetone, methyl ethyl ketone, 2-pentanone, 3-pentanone, 2-hexanone or methyl isobutyl ketone may, for example, be mentioned.

As the ester, methyl acetate, ethyl acetate, butyl acetate, methyl propionate, methyl lactate, ethyl lactate or pentyl lactate may, for example, be mentioned.

As the ether, diisopropyl ether, dioxane or tetrahydrofuran may, for example, be mentioned.

As the radical polymerization initiator, a commonly used initiator such as an azo type polymerization initiator, a peroxide type polymerization initiator or a redox type initiator may be used depending upon the polymerization temperature. As the radical polymerization initiator, an azo type compound is particularly preferred, and in a case where the polymerization is carried out in an aqueous medium, a salt of an azo type compound is more preferred.

The amount of the polymerization initiator to be added is preferably from 0.05 to 5 parts by mass, more preferably from 0.1 to 3 parts by mass, per 100 parts by mass of the monomer.

At the time of polymerization of a monomer, a molecular weight-adjusting agent may be used. As the molecular weight-adjusting agent, an aromatic compound, a mercapto alcohol or a mercaptan is preferred, and an alkyl mercaptan is particularly preferred. As such a molecular weight-adjusting agent, specifically, mercapto ethanol, n-octyl mercaptan, n-dodecyl mercaptan, t-dodecyl mercaptan or stearyl mercaptan may, for example, be mentioned.

The amount of the molecular weight-adjusting agent to be added is preferably from 0.01 to 5 parts by mass, more preferably from 0.1 to 3 parts by mass, per 100 parts by mass of the monomer.

The polymerization temperature is preferably from 20 to 150° C. As other polymerization conditions, conditions similar to ones used for polymerization for a usual (meth)acrylate type polymer may be applied. For example, the polymerization may be carried out in a nitrogen atmosphere, or an operation such as shaking may be added, such being preferred conditions in the production method of the present invention. With respect to the polymerization time, the polymer of the present invention can be obtained by carrying out the polymerization for from about 2 to 24 hours, although it may depend also on other polymerization conditions such as the polymerization temperature.

Further, in order to obtain the polymer of the present invention to have the above-mentioned preferred molecular weight range i.e. a range of from 2,000 to 1,000,000, more preferably from 5,000 to 500,000, by mass average molecular weight (Mw), the conditions such as the monomer concentration, the amount of the polymerization initiator, the polymerization temperature, the amount of the molecular weight-adjusting agent, etc. may be adjusted within the above-described preferred ranges. In general, under such a polymerization condition that the monomer concentration is high (low), the amount of the polymerization initiator is small (large), the polymerization temperature is low (high) or the amount of the molecular weight-adjusting agent is small (large), the molecular weight tends to be large (small).

Although the reason is not clearly understood, in the polymer of the present invention, $R^F$ groups are surface-oriented on the surface of a coating film by an interaction due to π-π stacking of a benzene ring contained in the linking group of the fluorinated compound by using the fluorinated compound of the present invention as the monomer. By the surface orientation of $R^F$ groups, even by a monomer having an $R^F$ group with at most 6 carbon atoms, it is possible to impart a high water/oil repellency.

EXAMPLES

Now, Examples of the present invention will be given, but it should be understood that the present invention is by no means restricted by such Examples.

<1> Production of Fluorinated Compound

Example 1

Into a reactor (internal capacity: 1 L, made of glass) equipped with a stirrer and a Dimroth condenser, 4-(chloromethyl)benzyl chloride (100.0 g), linear C$_6$F$_{13}$CH$_2$CH$_2$OH (228.8 g), sodium hydroxide (27.4 g) and acetonitrile (500 mL) were put and stirred. Then, heating was carried out so that the inner temperature of the reactor became 80° C., and stirring was further continued for 5 hours.

The solvent in the obtained reaction crude liquid was distilled off, and further, the solid was filtered off to obtain 278 g of a crude product. This product was distilled to obtain 78.3 g of a compound (A-1) (boiling point: 133° C./0.7 kPa, colorless transparent liquid) represented by the following structural formula (A-1) and classified into the above compound (A). The yield was 27%.

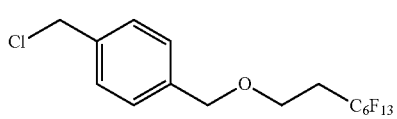

(A-1)

The measured results of $^1$H-NMR of the obtained compound (A-1) are shown below. Here, each measured value means a measured value derived from a group shown in ( ) following the measured value, but in a case where this group has a portion defined by [ ], the measured value means a measured value derived from the portion defined by [ ]. Hereinafter, the same applies to all of the measured results of NMR shown in Examples.

$^1$H-NMR (solvent: CDCl$_3$) δ(ppm): 2.45 (2H, m, —CH$_2$CF$_2$—), 3.77 (2H, t, —O[CH$_2$]CH$_2$CF$_2$—), 4.46 (2H, s, -Ph[CH$_2$]O—), 4.50 (2H, s, Cl[CH$_2$]Ph-), 7.31-7.40 (4H, m, Ph).

Into a reactor (internal capacity: 500 mL, made of glass) equipped with a stirrer and a Dimroth condenser, the compound (A-1) (78.0 g), 4-(2-hydroxyethyl)phenol (21.4 g), potassium carbonate (42.9 g) and DMF (250 mL) were put and stirred. Then, heating was carried out so that the inner temperature of the reactor became 80° C., and stirring was further continued for 6 hours.

The obtained reaction crude liquid was transferred to a separating funnel, chloroform (150 mL) was added, followed by washing three times with distilled water (100 mL), the solvent in the chloroform phase was distilled off, and the residue was recrystallized from 10 mass % methanol/hexane to obtain 72.3 g of a compound (B-1) (white solid) represented by the following structural formula (B-1) and classified into the above compound (B). The yield was 77%.

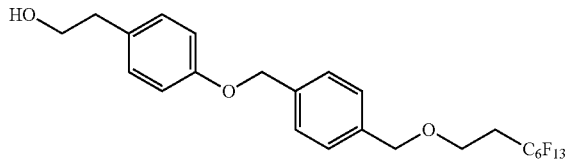

(B-1)

The measured results of $^1$H-NMR of the obtained compound (B-1) are shown below.

$^1$H-NMR (solvent: CDCl$_3$) δ(ppm): 1.34 (1H, t, —OH), 2.45 (2H, m, —CH$_2$CF$_2$—), 2.81 (2H, t, —CH$_2$[CH$_2$]PhO—), 3.75-3.86 (4H, m, —O[CH$_2$]CH$_2$CF$_2$— and HO[CH$_2$]CH$_2$—), 4.55 (2H, s, -Ph[CH$_2$]OCH$_2$—), 5.05 (2H, s, -PhO[CH$_2$]PhCH$_2$—), 6.92 (2H, d, Ph), 7.14 (2H, d, Ph), 7.35 (2H, d, Ph), 7.42 (2H, d, Ph).

Into a reactor (internal capacity: 50 mL, made of glass) equipped with a stirrer and a dropping funnel, the compound (B-1) (6.00 g), triethylamine (1.21 g) and dichloropentafluoropropane (tradename: AK-225, manufactured by Asahi Glass Company, Limited) (12 mL) were put and stirred. Then, by an ice bath, the internal temperature of the reactor was adjusted to be at most 10° C., and in a nitrogen atmosphere, acrylic acid chloride (1.00 g) was dropwise added. Further, the temperature was returned to room temperature, and stirring was continued for 2 hours.

The obtained reaction crude liquid was transferred to a separating funnel and washed three times with distilled water (10 mL), and the solvent in the AK-225 phase was distilled off to obtain 5.93 g of a fluorinated compound (I-1) of the present invention (white solid) having linear C$_6$F$_{13}$, represented by the following structural formula (I-1). The yield was 91%.

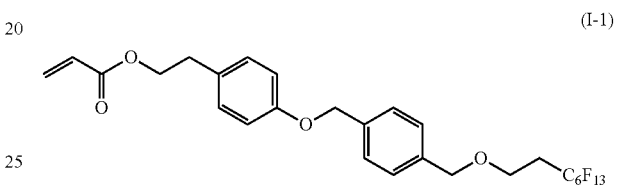

(I-1)

The measured results of $^1$H-NMR of the obtained fluorinated compound (I-1) of the present invention are shown below.

$^1$H-NMR (solvent: CDCl$_3$) δ(ppm): 2.45 (2H, m, —CH$_2$CF$_2$—), 2.92 (2H, t, —CH$_2$[CH$_2$]PhO—), 3.77 (2H, t, —O[CH$_2$]CH$_2$CF$_2$—), 4.33 (2H, t, —COO[CH$_2$]CH$_2$—), 4.55 (2H, s, -Ph[CH$_2$]OCH$_2$—), 5.05 (2H, s, -PhO[CH$_2$]PhCH$_2$—), 5.81 (1H, s, transC=CH$_2$), 6.11 (1H, dd, —CH=), 6.38 (1H, s, cisC=CH$_2$), 6.91 (2H, d, Ph), 7.14 (2H, d, Ph), 7.35 (2H, d, Ph), 7.42 (2H, d, Ph).

Example 2

Into a reactor (internal capacity: 50 mL, made of glass) equipped with a stirrer and a dropping funnel, the compound (B-1) disclosed in Example 1 (6.00 g), triethylamine (1.21 g) and AK-225 (12 mL) were put and stirred. Then, by an ice bath, the internal temperature of the reactor was adjusted to be at most 10° C., and in a nitrogen atmosphere, methacrylic acid chloride (1.14 g) was dropwise added. Further, the temperature was returned to room temperature, and stirring was continued for 2 hours.

The obtained reaction crude liquid was transferred to a separating funnel and washed three times with distilled water (10 mL), and the solvent in the AK-225 phase was distilled off to obtain 5.47 g of a fluorinated compound (1-2) of the present invention (white solid) having linear C$_6$F$_{13}$, represented by the following structural formula (I-2). The yield was 82%.

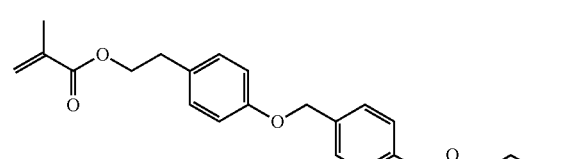

(I-2)

The measured results of $^1$H-NMR of the obtained fluorinated compound (I-2) of the present invention are shown below.

$^1$H-NMR (solvent: CDCl$_3$) δ(ppm): 1.93 (3H, s, CH$_3$—), 2.45 (2H, m, —CH$_2$CF$_2$—), 2.92 (2H, t, —CH$_2$[CH$_2$]PhO—), 3.77 (2H, t, —O[CH$_2$]CH$_2$CF$_2$—), 4.31 (2H, t, —COO[CH$_2$]CH$_2$—), 4.55 (2H, s, -Ph[CH$_2$]OCH$_2$—), 5.04 (2H, s, -PhO[CH$_2$]PhCH$_2$—), 5.54 (1H, s, transC=CH$_2$), 6.08 (1H, s, cisC=CH$_2$), 6.91 (2H, d, Ph), 7.14 (2H, d, Ph), 7.35 (2H, d, Ph), 7.42 (2H, d, Ph).

Example 3

Into a reactor (internal capacity: 300 mL, made of glass) equipped with a stirrer and a dropping funnel, linear C$_6$F$_{13}$CH$_2$CH$_2$OH (45.9 g), triethylamine (15.3 g) and acetone (100 mL) were put and stirred. Then, by an ice bath, the inner temperature of the reactor was adjusted to be at most 10° C., and in a nitrogen atmosphere, a solution of 4-(chloromethyl)benzoic acid chloride (25.0 g) in acetone (20 mL) was dropwise added. Further, the temperature was returned to room temperature, and stirring was continued for 2 hours.

The obtained reaction crude liquid was transferred to a separating funnel, dichloropentafluoropropane (tradename: AK-225, manufactured by Asahi Glass Company, Limited) (200 mL) was added, followed by washing three times with distilled water (200 mL), and the solvent in the AK-225 phase was distilled off to obtain 65.0 g of a compound (C-1) (white solid) represented by the following structural formula (C-1) and classified into the above compound (C). The yield was 95%.

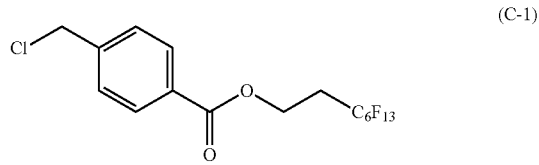

(C-1)

The measured results of $^1$H-NMR of the obtained compound (C-1) are shown below.

$^1$H-NMR (solvent: CDCl$_3$) δ(ppm): 2.62 (2H, m, —CH$_2$CF$_2$—), 4.62 (2H, s, ClCH$_2$—), 4.64 (2H, t, —OCH$_2$—), 7.48 (2H, d, Ph), 8.03 (2H, d, Ph).

Into a reactor (internal capacity: 500 mL, made of glass) equipped with a stirrer and a Dimroth condenser, the compound (C-1) (30.0 g), 4-(2-hydroxyethyl)phenol (8.02 g), potassium carbonate (16.1 g) and DMF (100 mL) were put and stirred. Then, heating was carried out so that the inner temperature of the reactor became 80° C., and stirring was further carried out for 6 hours.

The obtained reaction crude liquid was transferred to a separating funnel, chloroform (200 mL) was added, followed by washing three times with distilled water (200 mL), and the solvent in the chloroform phase was distilled off to obtain 27.7 g of a compound (D-1) (white solid) represented by the following structural formula (D-1) and classified into the above compound (D). The yield was 77%.

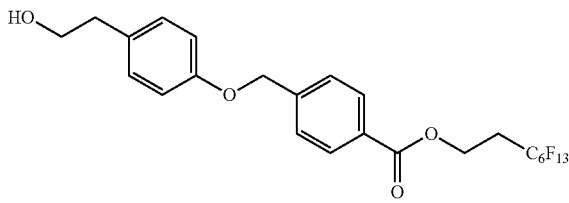

(D-1)

The measured results of $^1$H-NMR of the obtained compound (D-1) are shown below.

$^1$H-NMR (solvent: CDCl$_3$) δ(ppm): 2.61 (2H, m, —CH$_2$CF$_2$—), 2.82 (2H, t, —CH$_2$[CH$_2$]PhO—), 3.83 (2H, t, HO[CH$_2$]CH$_2$—), 4.63 (2H, t, —COO[CH$_2$]CH$_2$CF$_2$—), 5.12 (2H, s, -PhO[CH$_2$]Ph-), 6.91 (2H, d, Ph), 7.15 (2H, d, Ph), 7.51 (2H, d, Ph), 8.05 (2H, d, Ph).

Into a reactor (internal capacity: 50 mL, made of glass) equipped with a stirrer and a dropping funnel, the compound (D-1) (10.0 g), triethylamine (1.96 g) and methylene chloride (20 mL) were put and stirred. Then, by an ice bath, the inner temperature of the reactor was adjusted to be at most 10° C., and in a nitrogen atmosphere, acrylic acid chloride (1.61 g) was dropwise added. Further, the temperature was returned to room temperature, and stirring was continued for 2 hours.

The obtained reaction crude liquid was transferred to a separating funnel and washed three times with distilled water (20 mL), the solvent in the methylene chloride phase was distilled off, and the residue was recrystallized from 67 mass % methanol/AK-225 to obtain 7.10 g of a fluorinated compound (I-3) of the present invention (white solid) having linear C$_6$F$_{13}$, represented by the following structural formula (I-3). The yield was 65%.

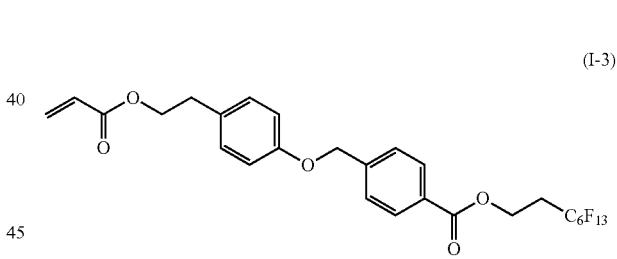

(I-3)

The measured results of $^1$H-NMR of the obtained fluorinated compound (I-3) of the present invention are shown below.

$^1$H-NMR (solvent: CDCl$_3$) δ(ppm): 2.62 (2H, m, —CH$_2$CF$_2$—), 2.92 (2H, t, —CH$_2$[CH$_2$]PhO—), 4.33 (2H, t, —COO[CH$_2$]CH$_2$Ph-), 4.63 (2H, t, —COO[CH$_2$]CH$_2$CF$_2$—), 5.12 (2H, s, -PhO[CH$_2$]Ph-), 5.82 (1H, s, transC=CH$_2$), 6.11 (1H, dd, —CH=), 6.38 (1H, s, cisC=CH$_2$), 6.90 (2H, d, Ph), 7.15 (2H, d, Ph), 7.51 (2H, d, Ph), 8.05 (2H, d, Ph).

Example 4

Into a reactor (internal capacity: 50 mL, made of glass) equipped with a stirrer and a dropping funnel, the compound (D-1) disclosed in Example 3 (10.0 g), triethylamine (1.96 g) and methylene chloride (20 mL) were put and stirred. Then, by an ice bath, the inner temperature of the reactor was adjusted to be at most 10° C., and in a nitrogen atmosphere, methacrylic acid chloride (1.86 g) was dropwise added. Further, the temperature was returned to room temperature, and stirring was continued for 2 hours.

The obtained reaction crude liquid was transferred to a separating funnel and washed three times with distilled water (20 mL), the solvent in the methylene chloride phase was distilled off, and the residue was recrystallized from 67 mass % methanol/AK-225 to obtain 6.52 g of a fluorinated compound (I-4) of the present invention (white solid) having linear $C_6F_{13}$, represented by the following structural formula (I-4). The yield was 59%.

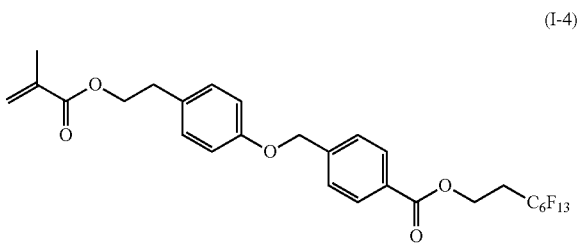

(I-4)

The measured results of $^1$H-NMR of the obtained fluorinated compound (I-4) of the present invention are shown below.

$^1$H-NMR (solvent: $CDCl_3$) δ(ppm): 1.92 (3H, s, $CH_3$—), 2.62 (2H, m, —$CH_2CF_2$—), 2.92 (2H, t, —$CH_2[CH_2]$PhO—), 4.31 (2H, t, —COO[$CH_2$]$CH_2$Ph-), 4.63 (2H, t, —COO[$CH_2$]$CH_2CF_2$—), 5.12 (2H, s, -PhO[$CH_2$]Ph-), 5.45 (1H, s, transC=$CH_2$), 6.08 (1H, s, cisC=$CH_2$), 6.90 (2H, d, Ph), 7.15 (2H, d, Ph), 7.51 (2H, d, Ph), 8.05 (2H, d, Ph).

Example 5

Into a reactor (internal capacity: 200 mL, made of glass) equipped with a stirrer and a dropping funnel, linear $C_2F_5CH_2CH_2CH_2OH$ (23.6 g), triethylamine (16.1 g) and acetone (80 mL) were put and stirred. Then, by an ice bath, the inner temperature of the reactor was adjusted to be at most 10° C., and in a nitrogen atmosphere, a solution of 4-(chloromethyl)benzoic acid chloride (25.0 g) in acetone (15 mL) was dropwise added. Further, the temperature was returned to room temperature, and stirring was continued for 2 hours.

The obtained reaction crude liquid was transferred to a separating funnel, dichloropentafluoropropane (tradename: AK-225, manufactured by Asahi Glass Company, Limited) (100 mL) was added, followed by washing three times with distilled water (100 mL), and the solvent in the AK-225 phase was distilled off to obtain 40.2 g of a compound (C-2) (pale yellow liquid) represented by the following structural formula (C-2) and classified into the above compound (C). The yield was 93%.

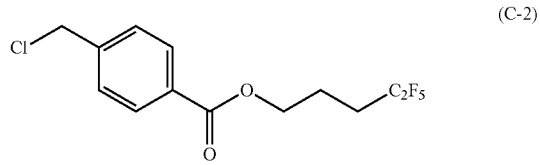

(C-2)

The measured results of $^1$H-NMR and $^{19}$F-NMR of the obtained compound (C-2) are shown below.

$^1$H-NMR (solvent: $CDCl_3$) δ(ppm): 2.05-2.31 (4H, m, —$CH_2[CH_2CH_2]CF_2$—), 4.41 (2H, t, —$OCH_2$—), 4.62 (2H, s, $ClCH_2$—), 7.48 (2H, d, Ph), 8.03 (2H, d, Ph).

$^{19}$F-NMR (solvent: $CDCl_3$) δ(ppm): -85.9 (3F, s, —$CF_3$), -118.7 (2F, t, —$CF_2$—).

Into a reactor (internal capacity: 100 mL, made of glass) equipped with a stirrer and a Dimroth condenser, the compound (C-2) (10.0 g), 4-(2-hydroxyethyl)phenol (4.18 g), potassium carbonate (8.36 g) and DMF (60 mL) were put and stirred. Then, heating was carried out so that the inner temperature of the reactor became 80° C., and stirring was further carried out for 3 hours.

The obtained reaction crude liquid was transferred to a separating funnel, chloroform (50 mL) was added, followed by washing three times with distilled water (50 mL), and the solvent in the chloroform phase was distilled off to obtain 12.2 g of a compound (D-2) (white solid) represented by the following structural formula (D-2) and classified into the above compound (D). The yield was 94%.

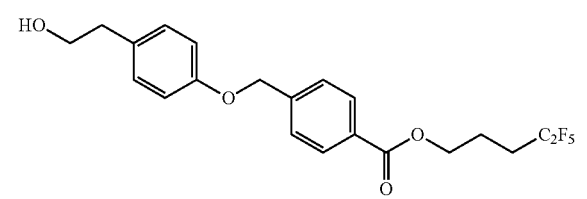

(D-2)

The measured results of $^1$H-NMR of the obtained compound (D-2) are shown below.

$^1$H-NMR (solvent: $CDCl_3$) δ(ppm): 1.47 (1H, s, —OH), 2.05-2.31 (4H, m, —$CH_2[CH_2CH_2]CF_2$—), 2.82 (2H, t, —$CH_2[CH_2]PhO$—), 3.82 (2H, q, HO[$CH_2$]$CH_2$—), 4.40 (2H, t, —COO[$CH_2$]$CH_2CH_2$—), 5.12 (2H, s, -PhO[$CH_2$]Ph-), 6.92 (2H, d, Ph), 7.15 (2H, d, Ph), 7.52 (2H, d, Ph), 8.04 (2H, d, Ph).

Into a reactor (internal capacity: 100 mL, made of glass) equipped with a stirrer and a dropping funnel, the compound (D-2) (12.0 g), triethylamine (3.37 g) and methylene chloride (30 mL) were put and stirred. Then, by an ice bath, the inner temperature of the reactor was adjusted to be at most 10° C., and in a nitrogen atmosphere, methacrylic acid chloride (3.19 g) was dropwise added. Further, the temperature was returned to room temperature, and stirring was continued for 2 hours.

The obtained reaction crude liquid was transferred to a separating funnel and washed three times with distilled water (30 mL), the solvent in the methylene chloride phase was distilled off, and the residue was recrystallized from hexane to obtain 8.05 g of a fluorinated compound (I-5) of the present invention (white solid) represented by the following structural formula (I-5). The yield was 59%.

(I-5)

The measured results of $^1$H-NMR and $^{19}$F-NMR of the obtained fluorinated compound (I-5) of the present invention are shown below.

$^1$H-NMR (solvent: CDCl$_3$) δ(ppm): 1.92 (3H, s, CH$_3$—), 2.05-2.31 (4H, m, —CH$_2$[CH$_2$CH$_2$]CF$_2$—), 2.92 (2H, t, —CH$_2$[CH$_2$]PhO—), 4.31 (2H, t, —COO[CH$_2$]CH$_2$Ph-), 4.40 (2H, t, —COO[CH$_2$]CH$_2$CH$_2$—), 5.12 (2H, s, -PhO[CH$_2$]Ph-), 5.54 (1H, s, transC=CH$_2$), 6.08 (1H, s, cisC=CH$_2$), 6.90 (2H, d, Ph), 7.15 (2H, d, Ph), 7.51 (2H, d, Ph), 8.04 (2H, d, Ph).

$^{19}$F-NMR (solvent: CDCl$_3$) δ(ppm): −85.9 (3F, s, —CF$_3$), −118.7 (2F, t, —CF$_2$—).

<2> Production of Polymer

Examples 6 to 10

Using the fluorinated compounds (I-1 to I-5) obtained in the above Examples as monomers, respectively, polymers were produced as follows.

Into a 30 mL glass ampoule for polymerization, a monomer, 2,2'-azobisisobutyronitrile as an initiator and AK-225 or a mixture of AK-225 and tetrahydrofuran (THF) as a solvent were put in the amounts as shown in Table 1. The gas in the interior of the ampoule was substituted by nitrogen gas, and then, the ampoule was sealed and maintained for 16 hours in a hot bath of 60° C. The solution containing the polymer was dropped into methanol of 20 times by mass, followed by stirring to let solid precipitate. The obtained solid was collected by filtration and vacuum-dried overnight at 60° C. to obtain a polymer in the amount shown by mass in Table 1. The molecular weight of the recovered polymer was measured by GPC. The mass average molecular weight (Mw) of the obtained polymer is shown in Table 1.

Here, the above mass average molecular weight (Mw) was measured by the following GPC measuring method.

(GPC Measuring Method)

The recovered polymer was dissolved in a mixed solvent of a fluorinated solvent (AK-225, manufactured by Asahi Glass Company, Limited)/hexafluoroisopropyl alcohol=99/1 (volume ratio) to obtain a 0.5 mass % solution, which was passed through a filter of 0.2 μm to obtain an analytical sample. With respect to such a sample, the number average molecular weight (Mn) and the mass average molecular weight (Mw) were measured. The measuring conditions were as follows.
Apparatus: HLC-8220GPC, manufactured by TOSOH CORPORATION,
Column: Two MIXED-E, manufactured by Polymer Laboratories, were connected in series,
Temperature for measurement: 37° C.,
Amount injected: 50 μL,
Exit velocity: 1 mL/min,
Standard sample: EasiCal PM-2, manufactured by Polymer Laboratories,
Eluent: Mixed solvent of fluorinated solvent (AK-225, manufactured by Asahi Glass Company, Limited)/hexafluoroisopropyl alcohol=99/1 (volume ratio).

TABLE 1

| Ex. No. | Monomer Symbol | Monomer Mass (g) | Initiator Mass (mg) | solvent Symbol | solvent Mass (g) | Polymer Yield (g) | Polymer Mw |
|---|---|---|---|---|---|---|---|
| Ex. 6 | I-1 | 5.00 | 19 | AK-225 | 20.0 | 3.81 | 44,000 |
| 7 | I-2 | 5.00 | 18 | AK-225 | 20.0 | 4.08 | 185,000 |
| 8 | I-3 | 5.00 | 12 | AK-225 | 20.0 | 3.75 | 60,000 |
| 9 | I-4 | 5.00 | 12 | AK-225 | 20.0 | 4.42 | 61,000 |
| 10 | I-5 | 4.00 | 13 | 225/THF | 16.0 | 3.59 | 82,000 |

Here, an abbreviation of the compound in Table 1 has the following meaning. 225/THF: A mixed solvent of AK-225 (50 mass %) and THF (50 mass %)

<Evaluation>

With respect to each of the polymers obtained in Examples 6 to 10, a test plate was prepared by the following method, and the water/oil repellency was evaluated. The results are shown in Table 2.

[Preparation of Test Plate]

A obtained polymer was diluted with AK-225 so that the solid content concentration became 2.0 mass %, and the obtained polymer solution was used as a treating liquid. The polymer solution was applied by dip coating to three glass plates and dried at 150° C. for 10 minutes to obtain treated substrates each having a coating film formed on the surface.

[Water/Oil Repellency]

Using one of the above treated substrates, the contact angles of water and hexadecane on the coating film were measured, whereby the water/oil repellency of the coating film obtainable from the treating liquid containing the polymer prepared in each of the above Examples, was evaluated. Here, the measurements of the contact angles were carried out by means of CA-X, manufactured by Kyowa Interface Science Co., Ltd. As results, the actually measured values of the contact angles as well as the results evaluated in accordance with the following standards, are shown.

The water repellency was evaluated by three grades using the contact angle of water being 100° as the standard.

⊚ (contact angle: at least 110°): Excellent in water repellency

○ (contact angle: at least 100° and less than 110°): Water repellency observed

× (contact angle: less than 100°): Inadequate in water repellency

The oil repellency was evaluated by three grades using the contact angle of n-hexadecane being 50° as the standard.

⊚ (contact angle: at least 70°): Excellent in oil repellency

○ (contact angle: at least 50° and less than 70°): Oil repellency observed

× (contact angle: less than 50°): Inadequate in oil repellency

[Dynamic Water Repellency]

Using one of the above treated substrates, the dynamic contact angles to water on the coating film was measured, whereby the dynamic water repellency of the coating film obtainable from the treating liquid containing a polymer prepared in each of the above Examples, was evaluated. Here, by means of DCAT21 (manufactured by DataPhysics), the receding contact angle to water was measured at 25° C. by Wilhelmy method. As results, the actually measured values of the receding contact angles as well as the results evaluated in accordance with the following standards, are shown.

The dynamic water repellency was evaluated by three grades using the receding contact angle of water being 50° as the standard.

⊚ (contact angle: at least 80°): Excellent in dynamic water repellency

○ (contact angle: at least 50° and less than 80°): Dynamic water repellency observed × (contact angle: less than 50°): Inadequate in dynamic water repellency

[Durability]

Using one of the above treated substrates, such a substrate was immersed for 3 hours in distilled water of 40° C., whereupon from the change rate between the receding contact angle where no treatment was carried out and the receding contact angle after the treatment, the durability of the dynamic water repellency of the coating film was evaluated. As results, the actually measured values of the receding contact angles after the immersion as well as the results evaluated in accordance with the following standards, are shown.

⊚ (change rate: less than 10%): Excellent in durability of dynamic water repellency ○ (change rate: at least 10% and less than 50%): Durability in dynamic water repellency observed × (change rate: at least 50%): Inadequate in durability of dynamic water repellency

TABLE 2

| | | Water/oil repellency | | | Dynamic water repellency | | | |
|---|---|---|---|---|---|---|---|---|
| | | | | | | | Receding | |
| | | | | | Receding | | | |
| Ex. No. | Contact angle (water) | Evaluation of water repellency | Contact angel (hexadecane) | Evaluation of oil repellency | contact angle (initial) | Evaluation of water repellency | contact angle (after immersion) | Evaluation of durability |
| Ex. 6 | 116 | ⊚ | 76 | ⊚ | 99 | ⊚ | 74 | ○ |
| 7 | 114 | ⊚ | 73 | ⊚ | 102 | ⊚ | 80 | ○ |
| 8 | 118 | ⊚ | 75 | ⊚ | 91 | ⊚ | 62 | ○ |
| 9 | 116 | ⊚ | 75 | ⊚ | 102 | ⊚ | 84 | ○ |
| 10 | 101 | ○ | 59 | ○ | 91 | ⊚ | 49 | ○ |

As is evident from Table 2, it is possible to obtain a polymer having a highly durable water/oil repellency by using the fluorinated compound of the present invention.

Industrial Applicability

The fluorinated compound of the present invention is a fluorinated compound having an $R^F$ group with at most 6 carbon atoms, which presents little environmental load, and a polymer obtainable by polymerizing it has a highly durable water/oil repellency. Accordingly, in place of a copolymer having an $R^F$ group with at least 8 carbon atoms presenting a high environmental load, it is useful for e.g. a water/oil repellent composition.

This application is a continuation of PCT Application No. PCT/JP2010/069516, filed Nov. 2, 2010, which is based upon and claims the benefit of priority from Japanese Patent Application No. 2009-252411 filed on Nov. 2, 2009. The contents of those applications are incorporated herein by reference in its entirety.

What is claimed is:

1. A fluorinated compound represented by the following formula (I):

wherein M is a hydrogen atom, a methyl group or a halogen atom, n is 1 or 2, each Ph is a phenylene group, X is $CH_2O$ or $OCH_2$, Z is a single bond, a $C_{1-4}$ alkylene group containing an etheric oxygen atom, or $COO(CH_2)_m$, wherein m is an integer of from 1 to 4, and r is an integer of from 1 to 6.

2. The fluorinated compound according to claim 1, wherein at least one Ph in the formula (I) is a 1,4-phenylene group.

3. The fluorinated compound according to claim 1, wherein r in the formula (I) is an integer of from 2 to 6.

4. The fluorinated compound according to claim 3, wherein r in the formula (I) is an integer of from 4 to 6.

5. The fluorinated compound according to claim 1, wherein the fluorinated compound represented by the formula (I) is a compound represented by any one of the following formulae (I-1) to (I-5):

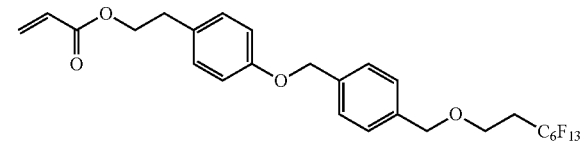

(I-1)

-continued

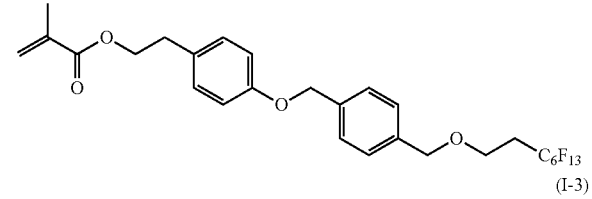

(I-2)

(I-3)

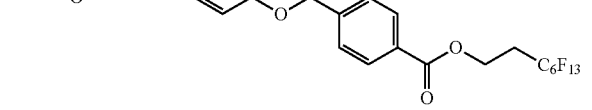

(I-4)

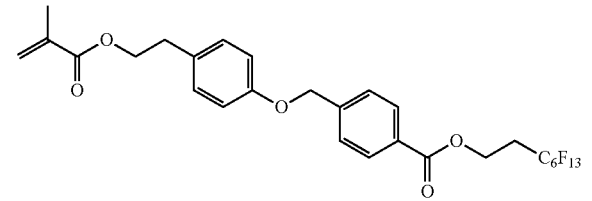

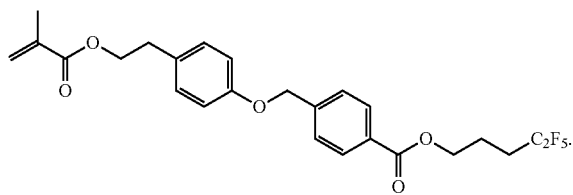

(I-5)

6. The fluorinated compound according to claim 1, wherein in the formula (I), r is an integer of from 4 to 6, and $C_rF_{2r+1}$ is linear.

7. The fluorinated compound according to claim 1, wherein each Ph in the formula (I) is a 1,4-phenylene group.

8. The fluorinated compound according to claim 1, wherein M in the formula (I) is a methyl group.

9. The fluorinated compound according to claim 1, wherein X in the formula (I) is $OCH_2$.

10. The fluorinated compound according to claim 1, wherein Z in the formula (I) is $-(CH_2)_p-O-(CH_2)_q-$, wherein p an integer of is from 0 to 2, and q is an integer of from 1 to 4, provided that p+q=1 to 4.

* * * * *